United States Patent
Doi et al.

(10) Patent No.: US 9,208,173 B1
(45) Date of Patent: *Dec. 8, 2015

(54) TECHNIQUES FOR MEDICAL IMAGE RETREIVAL

(71) Applicant: GLOBALFOUNDRIES U.S. 2 LLC, Malta, NY (US)

(72) Inventors: Munehiro Doi, Kanagawa (JP); Yumi Mori, Kanagawa-ken (JP); Hiroki Nakano, Shiga (JP)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/490,876

(22) Filed: Sep. 19, 2014

Related U.S. Application Data

(63) Continuation of application No. 14/365,325, filed on Jun. 13, 2014.

(51) Int. Cl.
*G06K 9/00* (2006.01)
*G06F 17/30* (2006.01)
(Continued)

(52) U.S. Cl.
CPC .... *G06F 17/30256* (2013.01); *G06F 17/30253* (2013.01); *G06F 19/321* (2013.01); *G06K 9/4604* (2013.01); *G06K 9/6215* (2013.01)

(58) Field of Classification Search
CPC ............ G06F 17/30256; G06F 19/321; G06F 17/30253; G06K 9/6215; G06K 9/4604
USPC ................................................ 382/128, 305
See application file for complete search history.

(56) References Cited

U.S. PATENT DOCUMENTS 6,292,577 B1 * 9/2001 Takahashi ...................... 382/128
8,009,936 B2 * 8/2011 Oosawa et al. ................ 382/305
(Continued)

FOREIGN PATENT DOCUMENTS

JP     H10326286 A     12/1998
JP     2002230518 A     8/2002
(Continued)

OTHER PUBLICATIONS

Uehara, et al,. Miracles: Multimedia Information Retrieval, Classification, and Exploration System, Fujitsu Laboratories, Ltd., The Institute of Electronics, Information and Communication Engineers, May 2000.

(Continued)

*Primary Examiner* — John Strege
(74) *Attorney, Agent, or Firm* — Russell Ng PLLC

(57) ABSTRACT

A technique for searching for an image includes calculating wavelet features of a plurality of images. A keyword included in radiographic interpretation information is extracted for each of the stored images. The calculated wavelet features and the extracted keywords are stored in association with the respective stored images. A newly taken image is acquired and a wavelet feature of the acquired image is calculated. A keyword included in radiographic interpretation information corresponding to the acquired image is extracted and a search for similar radiographic interpretation information from the stored keywords is performed. A wavelet feature-based spatial distance between the acquired image and each of images corresponding to the radiographic interpretation information found is calculated. A search result of any images for which the calculated wavelet feature-based spatial distance is shorter than a predetermined value is output, in ascending order of the calculated wavelet feature-based spatial distance.

3 Claims, 8 Drawing Sheets

(51) Int. Cl.
  *G06K 9/62* (2006.01)
  *G06K 9/46* (2006.01)
  *G06F 19/00* (2011.01)

(56) References Cited

U.S. PATENT DOCUMENTS

| | | | |
|---|---|---|---|
| 8,189,883 B2* | 5/2012 | Oosawa et al. | 382/128 |
| 8,380,013 B2* | 2/2013 | Hisanaga et al. | 382/305 |
| 2003/0179213 A1* | 9/2003 | Liu | 345/619 |
| 2004/0267740 A1* | 12/2004 | Liu et al. | 707/3 |
| 2005/0244082 A1* | 11/2005 | Yamatake | 382/305 |
| 2007/0201754 A1* | 8/2007 | Li | 382/240 |
| 2009/0097756 A1* | 4/2009 | Kato | 382/190 |
| 2011/0099032 A1* | 4/2011 | Miyasa et al. | 705/3 |
| 2012/0183191 A1* | 7/2012 | Nakamura | 382/128 |

FOREIGN PATENT DOCUMENTS

| | | |
|---|---|---|
| JP | 2004078939 A | 3/2004 |
| JP | 20060164008 A | 6/2006 |
| JP | 2008077163 A | 4/2008 |
| JP | 2009082443 A | 4/2009 |
| JP | 2011050040 A | 2/2011 |

OTHER PUBLICATIONS

International Application No. PCT/JP2012/074063, International Search Report.

Kikuchi, IEICE Technical Report, Institute of Electronics Information and Communication Engineers, vol. 100, No. 31, May 2, 2000.

* cited by examiner 1 1:0.64 2:0.49 3:0.32 4:1.68 5:7.97 6:5.90 7:1.09 8:0.37 9:0.59 10:0.21
11:0.40 12:1.43 13:4.32 14:3.55 15:0.90 16:0.61 17:0.43 18:0.13 19:0.80
20:1.62 21:2.18 22:1.67 23:0.59 24:0.65
2 1:0.46 2:0.53 3:0.71 4:2.90 5:10.51 6:8.30 7:1.99 8:0.52 9:0.71 10:0.42
11:0.47 12:2.37 13:6.74 14:4.89 15:1.50 16:0.55 17:0.64 18:0.27 19:0.15
20:1.33 31:3.93 22:2.37 23:1.12 24:0.44
3 1:0.20 2:0.41 3:1.15 4:3.43 5:13.40 6:9.19 7:1.56 8:0.29 9:0.58 10:0.58
11:0.96 12:2.80 13:9.97 14:7.08 15:2.04 16:0.63 17:0.65 18:0.41 19:0.80
20:2.77 21:8.63 22:5.33 23:2.09 24:0.86

FIG. 6

| SITE | LEFT LUNG FIELD, UPPER LOBE |
|---|---|
| SYMPTOM | NODULAR SHADOW |
| DISEASE NAME | SQUAMOUS CELL CARCINOMA SUSPECTED |
| ACTION | WORKUP BY HR-CT |

FIG. 7

TECHNIQUES FOR MEDICAL IMAGE RETREIVAL

This application is a continuation of application Ser. No. 14/365,325, entitled "TECHNIQUES FOR MEDICAL IMAGE RETRIEVAL," filed Jun. 13, 2014, which is a national stage of International Application No. PCT/JP2012/074063, entitled "TECHNIQUES FOR MEDICAL IMAGE RETRIEVAL," filed Sep. 20, 2012, which claims priority to Japanese Patent Application No. 2011-272174, filed Dec. 13, 2011. The disclosures of application Ser. No. 14/365,325 and International Application No. PCT/JP2012/074063 are hereby incorporated herein by reference in their entirety for all purposes.

BACKGROUND

The disclosure relates to image retrieval and, more specifically, to medical image retrieval of an image having high similarity to an acquired image from among a plurality of stored images.

In medical practice, it is important to recognize the internal states of a patient on the basis of images acquired by radiography. An X-ray image of a patient can be compared with X-ray images taken in the past to identify the causes of symptoms of the patient. This enables selection of appropriate medical treatment, leading to early improvement of the symptoms of the patient.

Japanese Unexamined Patent Publication No. 2005-237781 discloses a cardiomagnetometer which measures a cardiac magnetic signal and compares the measured cardiac magnetic signal with those measured in the past to determine whether the person is suffering from a cardiac disease or whether he/she is a candidate thereof. Japanese Unexamined Patent Publication No. 2008-077163 discloses a search system that calculates a similarity between a latest diagnosis image and each of diagnosis images included in past interpretation report data and, in consideration together with the rate of occurrence of a diagnosis result name in the past interpretation report data, searches for a past diagnosis image and the interpretation report data corresponding thereto.

In Japanese Unexamined Patent Publication No. 2005-237781, the determination is made on the basis of a cardiac magnetic signal, which is indirect information, and therefore an occurrence of a cardiac disease cannot be distinguished from an occurrence of any other disease indicated by a similar signal. In Japanese Unexamined Patent Publication No. 2008-077163, although the similarity between images is calculated by using a Euclidean distance between feature parts in the images, it is necessary to determine which part of the picked-up image is the feature part and, as such, the determination might depend on a doctor's skill in image reading.

BRIEF SUMMARY

A technique for searching for an image similar to a newly taken image, from among medical images based on past cases includes calculating wavelet features of a plurality of images that have been taken and stored in the past. A keyword included in radiographic interpretation information is extracted for each stored image. The calculated wavelet features and the extracted keywords are stored in association with the respective stored images. A newly taken image is acquired and a wavelet feature of the acquired image is calculated. A keyword included in radiographic interpretation information corresponding to the acquired image is extracted and, on the basis of the extracted keyword, a search for similar radiographic interpretation information from the stored keywords is performed. A wavelet feature-based spatial distance between the acquired image and each of images corresponding to the radiographic interpretation information found is calculated. A search result of any images for which the calculated wavelet feature-based spatial distance is shorter than a predetermined value is output, in ascending order of the calculated wavelet feature-based spatial distance.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

The above as well as additional objectives, features, and advantages of the present invention will become apparent in the following detailed written description.

BRIEF DESCRIPTION OF THE DRAWINGS

The description of the illustrative embodiments is to be read in conjunction with the accompanying drawings, wherein:

FIG. 6 shows, by way of example, the data structure of visual words stored in a visual word storage unit in a medical image search apparatus according to an embodiment of the present disclosure;

FIG. 7 shows, by way of example, keyword extraction by a medical image search apparatus according to an embodiment of the present disclosure;

DETAILED DESCRIPTION

Figure 1:
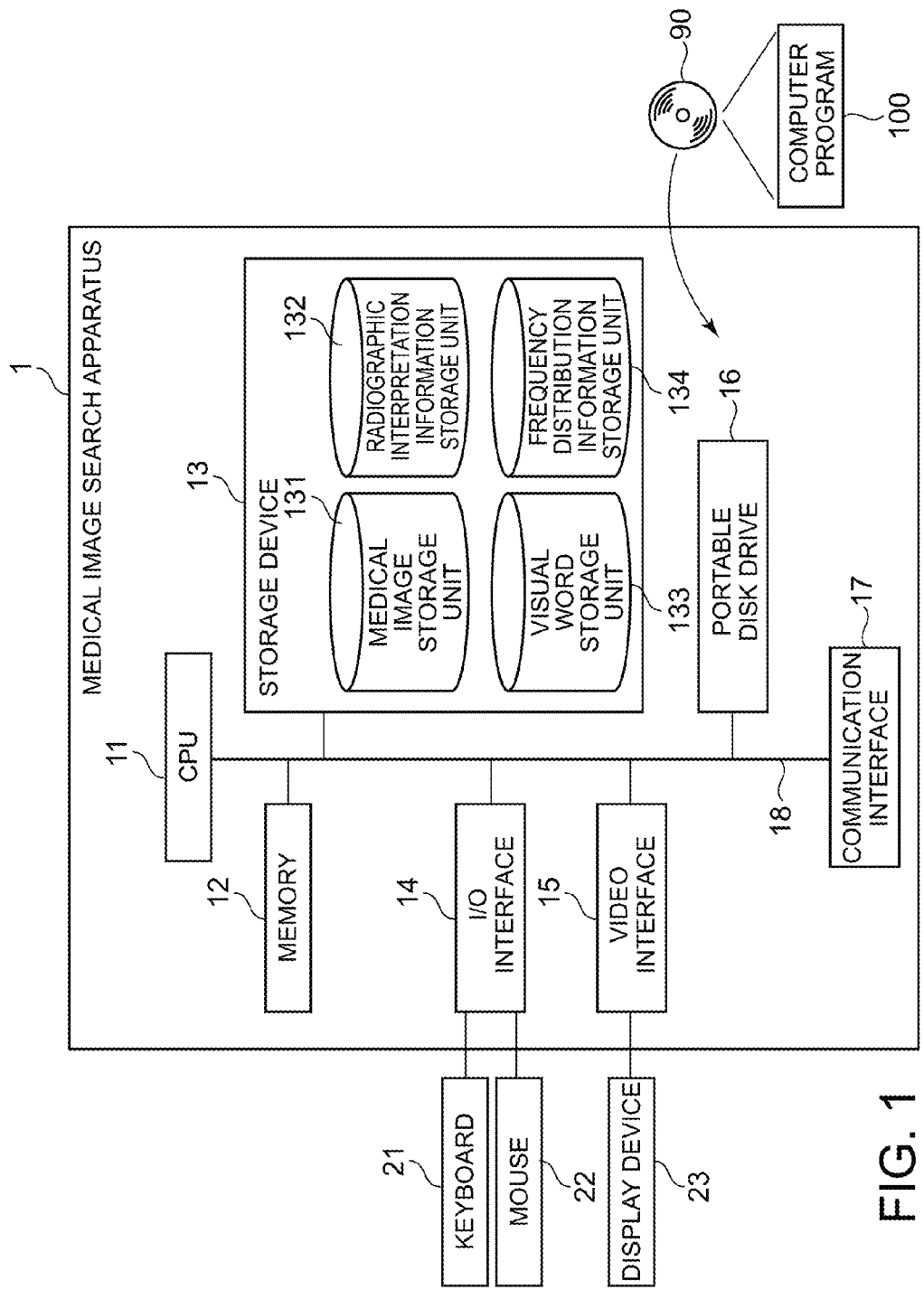
FIG. 1 is a block diagram schematically showing the configuration of a medical image search apparatus according to an embodiment of the present disclosure.

The illustrative embodiments provide a method, an apparatus, and a computer program product for retrieval of an image having high similarity to an acquired image, from among a plurality of stored images.

In the following detailed description of exemplary embodiments of the invention, specific exemplary embodiments in which the invention may be practiced are described in sufficient detail to enable those skilled in the art to practice the invention, and it is to be understood that other embodiments may be utilized and that logical, architectural, programmatic, mechanical, electrical and other changes may be made without departing from the spirit or scope of the present invention. The following detailed description is, therefore, not to be taken in a limiting sense, and the scope of the present invention is defined by the appended claims and equivalents thereof.

It should be understood that the use of specific component, device, and/or parameter names are for example only and not meant to imply any limitations on the invention. The invention may thus be implemented with different nomenclature/terminology utilized to describe the components/devices/parameters herein, without limitation. Each term utilized herein is to be given its broadest interpretation given the context in which that term is utilized. As may be used herein, the term 'coupled' may encompass a direct connection between components or elements or an indirect connection between components or elements utilizing one or more intervening components or elements.

Embodiments of the present disclosure are provided in view of the above background and provide a medical image search method, apparatus, and computer program capable of using a newly taken X-ray image to search with high accuracy for an existing image corresponding to a similar case.

A disclosed method, e.g., executed by a medical image search apparatus, searches for an image similar to a newly taken image from among medical images based on past cases. The method may include: calculating wavelet features of a plurality of images that have been taken and stored in the past; extracting a keyword included in the radiographic interpretation information for each stored image; storing the calculated wavelet features and the extracted keywords in association with the respective stored images; acquiring a newly taken image; calculating a wavelet feature of the acquired image; extracting a keyword included in radiographic interpretation information corresponding to the acquired image and, on the basis of the extracted keyword, searching for similar radiographic interpretation information from the stored keywords; calculating a wavelet feature-based spatial distance between the acquired image and each of images corresponding to the radiographic interpretation information found; and outputting as a search result any images the calculated spatial distance of which is shorter than a predetermined value, in ascending order of the spatial distance.

The method may include calculating a wavelet feature as a two-dimensional Gabor wavelet feature.

The method may further include calculating frequency distribution vectors for all images, by calculating M said wavelet features (M is a natural number of 2 or greater) for each image and binarizing the respective wavelet features for conversion into an M-dimensional bit string. The spatial distance may be calculated as an angle between the calculated frequency distribution vectors.

An apparatus, e.g., a medical image search apparatus, for searching for an image similar to a newly taken image, from among medical images based on past cases, may include: a feature calculation unit for calculating wavelet features of a plurality of images that have been taken and stored in the past; a keyword extraction unit for extracting a keyword included in radiographic interpretation information for each stored image; an information storage unit for storing the calculated wavelet features and the extracted keywords in association with the respective stored images; an image acquisition unit for acquiring a newly taken image; a wavelet feature calculation units for calculating a wavelet feature of the acquired image; a radiographic interpretation information search unit for extracting a keyword included in radiographic interpretation information corresponding to the acquired image and, on the basis of the extracted keyword, searching for similar radiographic interpretation information from the stored keywords; a spatial distance calculation unit for calculating a wavelet feature-based spatial distance between the acquired image and each of images corresponding to the radiographic interpretation information found; and an output unit for outputting as a search result any images the calculated spatial distance of which is shorter than a predetermined value, in ascending order of the spatial distance.

The feature calculation unit and the wavelet feature calculation unit may each calculate a two-dimensional Gabor wavelet feature as the wavelet feature.

The apparatus may further include a frequency distribution vector calculation unit for calculating frequency distribution vectors for all images, by calculating M said wavelet features (M is a natural number of 2 or greater) for each image and binarizing the respective wavelet features for conversion into an M-dimensional bit string, and the spatial distance calculation unit may calculate the spatial distance as an angle between the calculated frequency distribution vectors.

A computer program according, e.g., executable by a medical image search apparatus, may search for an image similar to a newly taken image, from among medical images based on past cases. The program causes an apparatus to function as: a feature calculation unit for calculating wavelet features of a plurality of images that have been taken and stored in the past; a keyword extraction unit for extracting a keyword included in radiographic interpretation information for each stored image; an information storage unit for storing the calculated wavelet features and the extracted keywords in association with the respective stored images; an image acquisition unit for acquiring a newly taken image; a wavelet feature calculation unit for calculating a wavelet feature of the acquired image; an interpretation information search unit for extracting a keyword included in radiographic interpretation information corresponding to the acquired image and, on the basis of the extracted keyword, searching for similar radiographic interpretation information from the stored keywords; a spatial distance calculation unit for calculating a wavelet feature-based spatial distance between the acquired image and each of images corresponding to the radiographic interpretation information found; and an output unit for outputting as a search result any images the calculated spatial distance of which is shorter than a predetermined value, in ascending order of the spatial distance.

The computer program according may cause the feature calculation unit and the wavelet feature calculation unit to calculate a two-dimensional Gabor wavelet feature as the wavelet feature.

The computer program may further causes the apparatus to function as a frequency distribution vector calculation unit for calculating frequency distribution vectors for all images, by calculating M said wavelet features (M is a natural number of 2 or greater) for each image and binarizing the respective wavelet features for conversion into an M-dimensional bit string, and the cause the spatial distance calculation unit to calculate the spatial distance as an angle between the calculated frequency distribution vectors.

According to the present disclosure, a wavelet feature indicating the feature of an acquired medical image can be used to search for a similar image from among the images stored as past cases. Even an inexperienced doctor is able to find an image corresponding to the most similar case and, thus, to select appropriate medical treatment.

A medical image search apparatus for searching for an image similar to a newly taken image, from among medical images based on past cases according to an embodiment of the present disclosure is specifically described below with reference to the drawings. The following embodiments do not restrict the claimed invention, and all the combinations of the features described in the embodiment are not necessarily indispensable.

Further, the present invention can be carried out in many different modes, and should not be understood only from the description given for the embodiment. Through the whole description of the embodiment, the same elements are denoted by the same reference numerals.

While an apparatus comprising a computer system having a computer program introduced therein will be described in the following embodiment, it should be apparent to those skilled in the art that part of the present invention may be implemented as a computer-executable computer program. Therefore, the present invention can take the form of an embodiment as hardware, e.g., a medical image search apparatus, that searches for an image similar to a newly taken image from among medical images based on past cases or an embodiment as a combination of software and hardware. The computer program may be recorded on an arbitrary computer-readable recording medium such as a hard disk, a DVD, a CD, an optical storage device, or a magnetic storage device.

According to an embodiment, a wavelet feature indicating the feature of an acquired medical image can be used to search for an image similar to the acquired image from among the images stored as past cases. Even an inexperienced doctor is able to find an image corresponding to the most similar case and, thus, to select appropriate medical treatment.

FIG. 1 is a block diagram schematically showing the configuration of a medical image search apparatus according to an embodiment. The medical image search apparatus 1 according to the embodiment at least includes: a central processing unit (CPU) or processor 11, a memory 12, a storage device 13, an I/O interface 14, a video interface 15, a portable disk drive 16, a communication interface 17, and an internal bus 18 for connecting the above-described hardware components.

The CPU 11 is connected via the internal bus 18 to the hardware components of the medical image search apparatus 1 as described above. The CPU 11 controls the operations of those hardware components, and also executes various software functions in accordance with a computer program 100 stored in the storage device 13. The memory 12 is made up of a volatile memory such as an SRAM or an SDRAM, in which a load module is deployed at the time of execution of the computer program 100. Temporary data generated during the execution of the computer program 100 is also stored in the memory 12.

The storage device 13 includes a built-in fixed storage (hard disk), a ROM, and others. The computer program 100 stored in the storage device 13 is one that has been downloaded by the portable disk drive 16 from a portable recording medium 90 such as a DVD or a CD-ROM that records information such as data and programs. At run-time, the computer program 100 is deployed from the storage device 13 to the memory 12 for execution. The computer program 100 may of course be downloaded from an external computer connected via the communication interface 17.

The storage device 13 includes a medical image storage unit 131, a radiographic interpretation information storage unit 132, a visual word storage unit 133, and a frequency distribution information storage unit 134. The medical image storage unit 131 stores image data of X-ray images taken in the past. The unit 131 stores the image data in association with identification information for identifying radiographic interpretation information.

The radiographic interpretation information storage unit 132 stores results of diagnoses that doctors have made by interpreting medical images taken in the past. For example, a doctor's diagnosis such as "nodular shadow found in left lung field, upper lobe; squamous cell carcinoma suspected; workup by HR-CT instructed" is stored in the form of text data in association with identification information.

The visual word storage unit 133 stores, as visual words, Gabor wavelet features which will be described later. The frequency distribution information storage unit 134 stores frequency distribution vectors of values obtained by binarizing calculated wavelet features and converting them into M-dimensional bit strings.

The communication interface 17 is connected to the internal bus 18, and to an external network such as the Internet, a LAN, or a WAN, so that it is able to transmit data to and receive data from an external computer and so on.

The I/O interface 14 is connected to input devices such as a keyboard 21 and a mouse 22, and accepts input of data. The video interface 15 is connected to a display device 23 such as a CRT display or a liquid crystal display, and displays a detected result on the display device 23.

Figure 2:
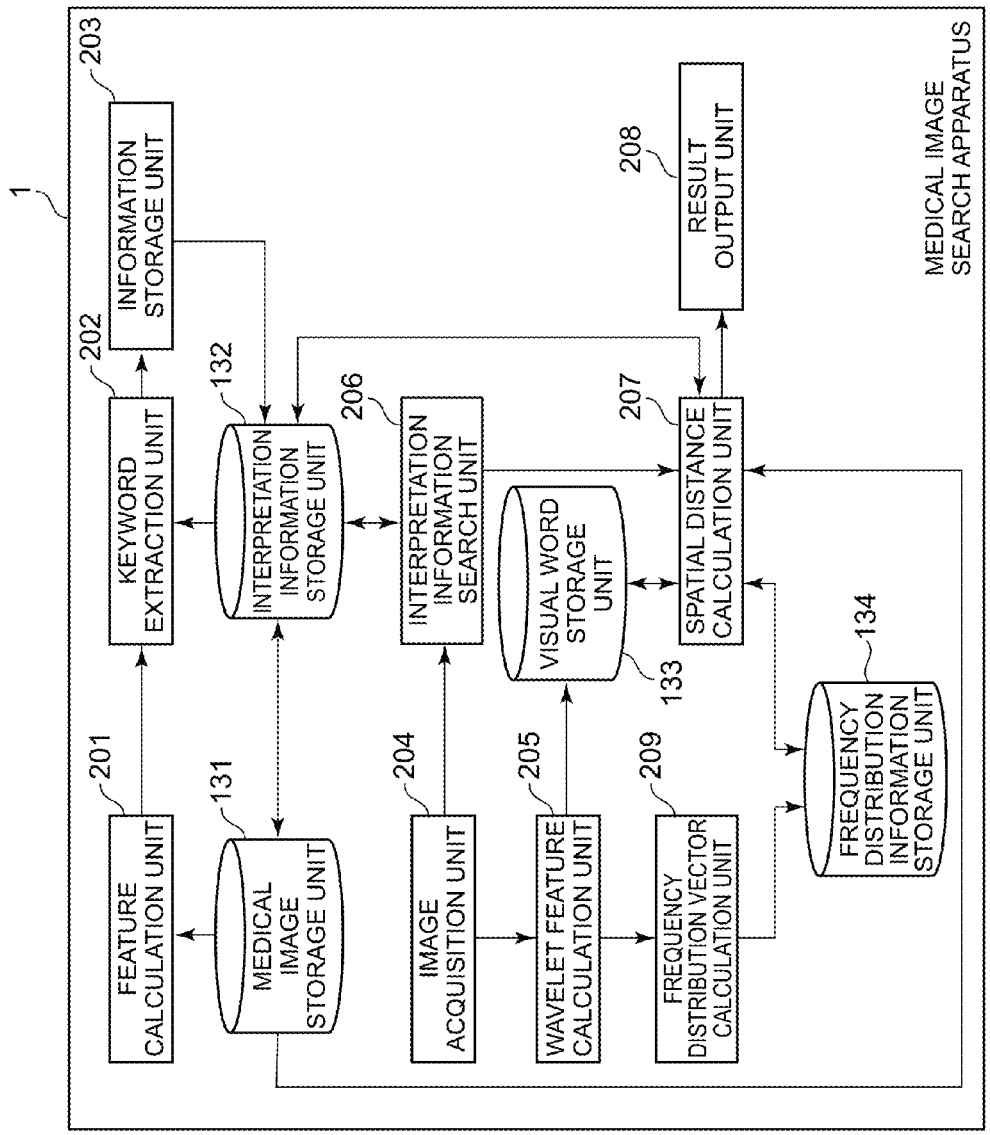
FIG. 2 is a functional block diagram of the medical image search apparatus according to an embodiment of the present disclosure.

FIG. 2 is a functional block diagram of the medical image search apparatus 1 according to an embodiment. In FIG. 2, a feature calculation unit 201 in the medical image search apparatus 1 calculates wavelet features of a plurality of images taken and stored in the past. In an embodiment, Gabor wavelet features are calculated as the wavelet features.

Figure 3:
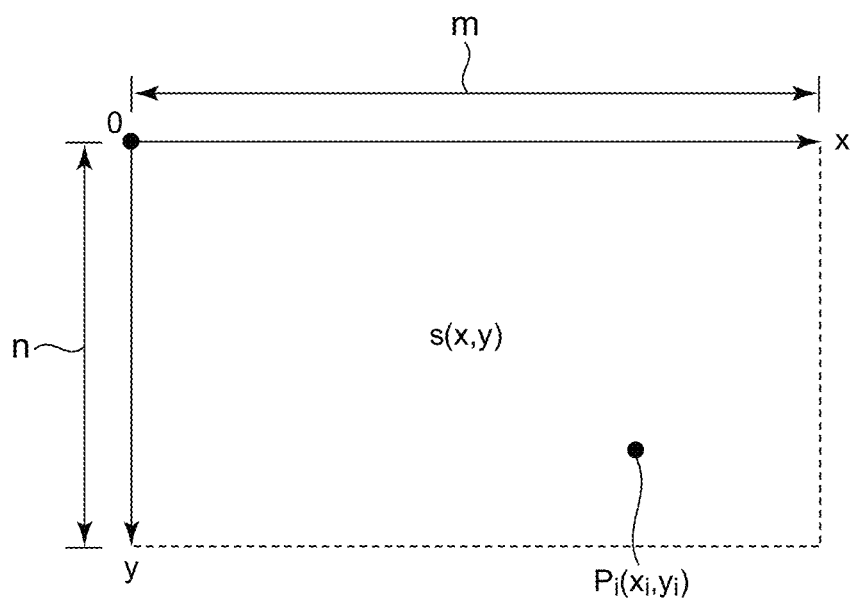
FIG. 3 illustrates coordinate setting within an image used in the medical image search apparatus according to an embodiment of the present disclosure.

FIG. 3 illustrates coordinate setting within an image used in the medical image search apparatus 1 according to an embodiment. As shown in FIG. 3, an image with an origin at an upper left corner thereof and having m pixels in an x direction and n pixels in a y direction is defined as s(x, y). The coordinates of an i-th pixel $P_i$ (i is a natural number) are represented as $P_i(x_i, y_i)$.

First, the coordinates $P_i(x_i, y_i)$ are affine-transformed to coordinates $(X_i, Y_i)$ in accordance with the following expression (1).

$$[X_i, Y_i, 1] = [x_i, y_i, 1]A \quad (1)$$

In the above expression (1), the matrix A is a 3×3 affine transformation matrix. The affine transformation to shift the entire image by tx in the x direction and by ty in the y direction can be expressed by the following expression (2), and the affine transformation to rotate the entire image by an angle θ can be expressed by the following expression (3).

$$[X_i, Y_i, 1] = [x_i, y_i, 1]\begin{bmatrix} 1 & 0 & 0 \\ 0 & 1 & 0 \\ tx & ty & 1 \end{bmatrix} \quad (2)$$

$$[X_i, Y_i, 1] = [x_i, y_i, 1]\begin{bmatrix} \cos\theta & \sin\theta & 0 \\ -\sin\theta & \cos\theta & 0 \\ 0 & 0 & 1 \end{bmatrix} \quad (3)$$

A two-dimensional Gabor wavelet function is defined, with respect to the coordinate values (x with dot, y with dot) after the affine transformation for rotation, as in the following expression (4).

$$\psi_r(x, y) = g_\sigma(\hat{x}, \hat{y})\left[e^{iu_0\hat{x}} - e^{-(u_0\sigma)^2}\right] \quad (4)$$

$$\begin{bmatrix} \hat{x} \\ \hat{y} \end{bmatrix} = \begin{bmatrix} \cos\theta_r & \sin\theta_r \\ -\sin\theta_r & \cos\theta_r \end{bmatrix} \begin{bmatrix} x \\ y \end{bmatrix}$$

Figure 4A:
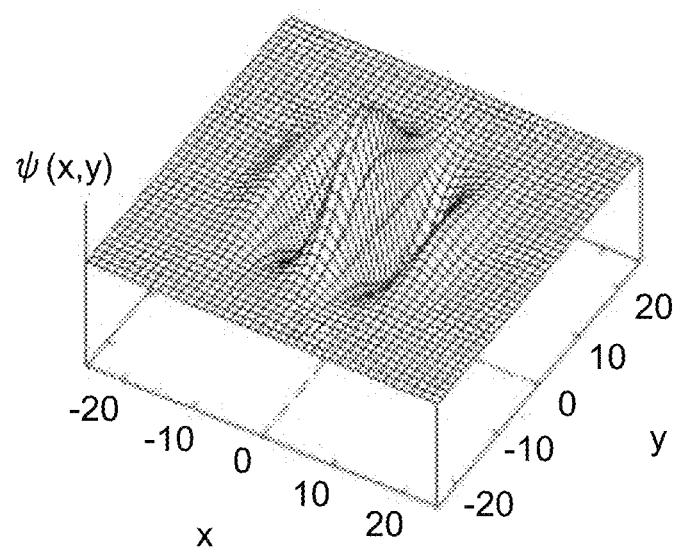
FIGS. 4A and 4B show, by way of example, a two-dimensional Gabor wavelet function.
Figure 4B:
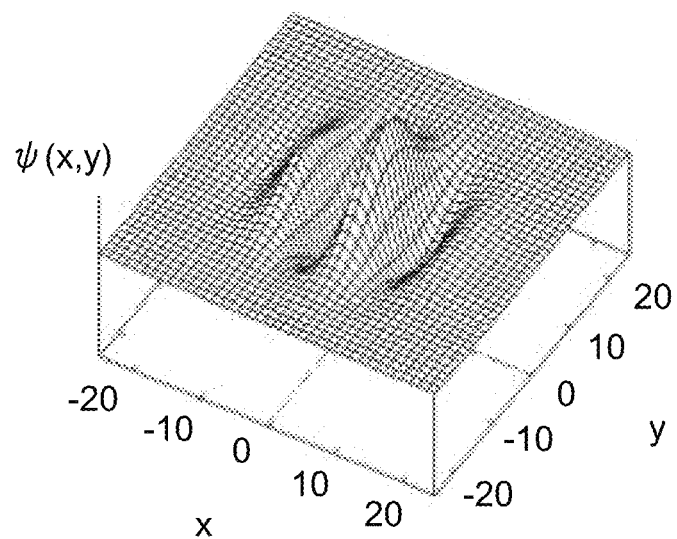

The two-dimensional Gabor wavelet function is composed of a real part and an imaginary part. FIGS. 4A and 4B show an example of a two-dimensional Gabor wavelet function. Specifically, FIGS. 4A and 4B show examples of the real part and imaginary part, respectively, of the two-dimensional Gabor wavelet function. As seen from FIGS. 4A and 4B, the real part of the two-dimensional Gabor wavelet function has a hat-like wavy form with its maximum value located near $(x, y)=(0, 0)$. In the above expression (4), $u_0$ represents the frequency of that waveform, and $\sigma$ represents the width of that hat shape. Further, r represents the direction, which will be described later.

The window function $g_\sigma$ in the above expression (4) is a two-dimensional Gaussian function, which can be expressed by the following expression (5).

$$g_\sigma(\hat{x}, \hat{y}) = \frac{1}{4\pi\sigma}e^{\frac{-1}{4\sigma^2}(\hat{x}^2+\hat{y}^2)} \quad (5)$$

Using the two-dimensional Gabor wavelet function, the Gabor wavelet features for an acquired image $s(x, y)$ can be calculated by the following expression (6). The lattice point at which the absolute value of the Gabor wavelet feature has a maximum value and the Gabor wavelet features in the vicinity of that lattice point are invariant even when the image is subjected to affine transformation such as scaling, rotation, etc., so that they are suitably used as the feature values of an image.

$$G_{j,r}(x_0, y_0) = a^{-j} \int\int s(x, y)\psi_r\left(\frac{x-x_0}{a^j}, \frac{y-y_0}{a^j}\right) dx dy \quad (6)$$

In the above expression (6), $a^j$ and $a^{-j}$ are parameters indicating the degrees of dilation (scaling), and $x_0$ and $y_0$ represent shift. Further, r represents the direction. In the present embodiment, the Gabor wavelet features in eight directions are calculated.

Figure 5:
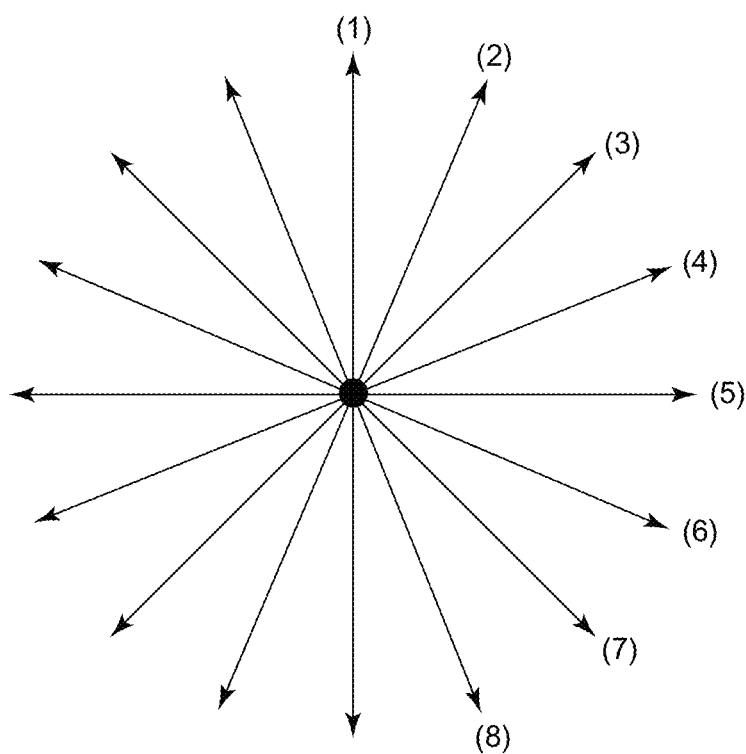
FIG. 5 is a schematic diagram showing the directions of the two-dimensional Gabor wavelet function used in a medical image search apparatus according to an embodiment of the present disclosure.

FIG. 5 is a schematic diagram showing the directions of the two-dimensional Gabor wavelet function used in the medical image search apparatus 1 according to an embodiment. As shown in FIG. 5, the Gabor wavelet features are calculated in directions (1) to (8), i.e. in eight directions spaced every 22.5 degrees from a prescribed direction.

The calculation of the Gabor wavelet features makes it possible to calculate the wavelet feature values that accommodate or absorb variations in shape of the human organs, for example, thereby enabling a high-precision search for a similar image.

For example, in the case where the above expression (6) is used to calculate the Gabor wavelet features for each coordinate point (x, y) (lattice point within an image), eight directions (r=1 to 8) and five scales (j=1 to 5) are selected to calculate 40 Gabor wavelet features for one coordinate point. Here, the scales 1 to 5 indicate the levels of enlargement/reduction. For example, a greater value indicates a greater degree of enlargement. From the Gabor wavelet features calculated, those having the absolute values of not less than a predetermined threshold value are extracted, and the Gabor wavelet feature having a maximum value among them is selected.

The fact that the absolute value of the Gabor wavelet feature takes a maximum value means that the absolute value of the integral in the above expression (6) is maximum. The feature value remains unchanged even when the average brightness of the image is changed, the scale of the image is changed, or the image is rotated.

In the present embodiment, the Gabor wavelet features in eight directions in the scale where a maximum value is obtained, as well as the Gabor wavelet features in the eight directions in each of the preceding and succeeding scales, namely 24 (3 scales×8 directions) Gabor wavelet features in total, are stored as a set of visual words in the visual word storage unit 133.

FIG. 6 shows, by way of example, the data structure of visual words stored in the visual word storage unit 133 in the storage device 13 in the medical image search apparatus 1 according to an embodiment. As shown in FIG. 6, 24 Gabor wavelet features which have been calculated are listed and stored corresponding to each identification number 1, 2, 3, . . . . More specifically, "1" at the beginning is the identification number, which is followed by a blank space, and the numerical values following "1:" to "24:" are the 24 Gabor wavelet features calculated. FIG. 6 shows the visual words in the case where there are three maximum values within one image. Thus, in FIG. 6, the visual words are stored corresponding to three identification numbers "1", "2", and "3". When there is one maximum value, there is naturally only one identification number "1".

Returning to FIG. 2, a keyword extraction unit 202 extracts keywords that are included in the radiographic interpretation information stored in the radiographic interpretation information storage unit 132 in the storage device 13 corresponding to the past images stored in the medical image storage unit 131 in the storage device 13. For example, in the case where radiographic interpretation information reading: "nodular shadow found in left lung field, upper lobe; squamous cell carcinoma suspected; workup by HR-CT instructed" is stored in the radiographic interpretation information storage unit 132 in the storage device 13, syntax analysis is carried out using morphological analysis or the like to extract keywords, which are classified as "site", "symptom", "disease name", "action", etc.

FIG. 7 shows, by way of example, keyword extraction by the medical image search apparatus 1 according to one embodiment. In the example shown in FIG. 7, through the syntactic analysis of "nodular shadow found in left lung field, upper lobe; squamous cell carcinoma suspected; workup by HR-CT instructed", the following keywords have been extracted: "left lung field, upper lobe" as "site", "nodular shadow" as "symptom", "squamous cell carcinoma suspected" as "disease name", and "workup by HR-CT" as "action".

An information storage unit 203 stores the wavelet features calculated in the above-described manner and the extracted keywords, as visual words, in the visual word storage unit 133 in the storage device 13. The unit 203 stores the wavelet features and the keywords in association with the past images stored in the medical image storage unit 131 in the storage device 13.

An image acquisition unit 204 acquires a newly taken image. The image acquisition unit 204 preferably acquires the radiographic interpretation information corresponding thereto at the same time. This can help narrowing down the images to be searched for a similar image.

A wavelet feature calculation unit 205 calculates wavelet features of the acquired image, similarly as in the above-described manner, and stores the calculated features as visual words in the visual word storage unit 133.

A radiographic interpretation information search unit 206 extracts at least one keyword included in the radiographic interpretation information for the acquired image and, on the basis of the extracted keyword, searches for similar radiographic interpretation information from the keywords stored in the radiographic interpretation information storage unit 132 in the storage device 13. In this manner, it is possible to effectively narrow down the images to be searched for a similar image.

A spatial distance calculation unit 207 calculates a wavelet feature-based spatial distance between the acquired image and an image corresponding to the radiographic interpretation information found. More specifically, for each pixel, M wavelet features (M is a natural number of 2 or greater), for example 24 wavelet features, are calculated, which are then binarized and converted to an M-dimensional bit string (M=24).

A frequency distribution vector calculation unit 209 generates a histogram indicating the frequency distribution of the values of the 24-dimensional bit strings obtained through conversion. Such a histogram is generated, not only for a newly acquired image, but also for all the images stored in the medical image storage unit 131, or for the images corresponding to the radiographic interpretation information found by the radiographic interpretation information search unit 206.

Figure 8:
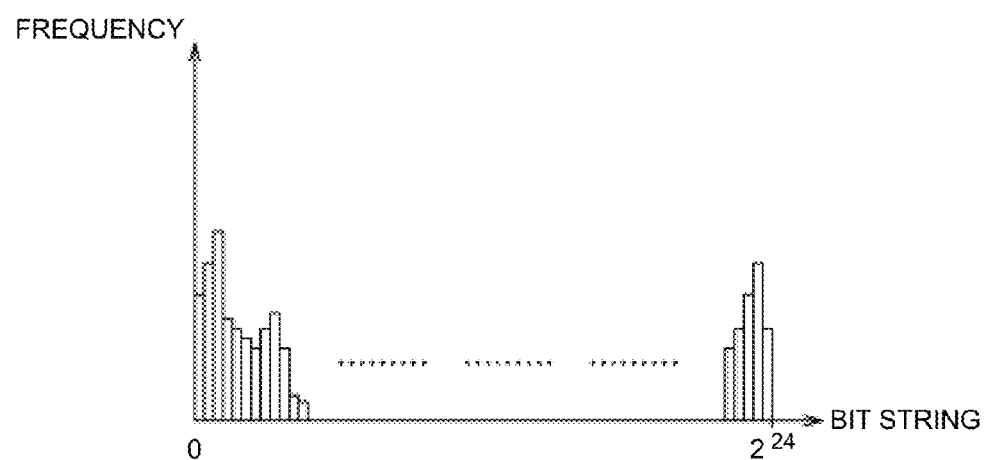
FIG. 8 shows, by way of example, a histogram according to an embodiment of the present disclosure.

FIG. 8 shows an example of a histogram according to one embodiment. In this example, $2^{24}$ values are taken along the horizontal axis, and frequency distribution is obtained for the respective values. The frequency distribution for each image can be used as a frequency distribution vector, to effectively narrow down the images to be searched for a similar image. The information regarding the generated histograms is stored in the frequency distribution information storage unit 134 in the storage device 13.

The spatial distance calculation unit 207 calculates the spatial distance between the newly acquired image and an image stored in the medical image storage unit 131, as an angle between the calculated frequency distribution vectors. More specifically, when the frequency distribution vector of the newly acquired image is represented as $V_1$ and the frequency distribution vector of an image stored in the medical image storage unit 131 is represented as $V_2$, then the spatial distance is calculated as the cosine of the angle $\phi$ between the two vectors, i.e. cos $\phi$, in accordance with the following expression (7).

$$\cos\phi = \frac{\langle V_1, V_2 \rangle}{\|V_1\| \cdot \|V_2\|} \qquad (7)$$

In the above expression (7), $\langle V_1, V_2 \rangle$ indicates the inner product of the vectors $V_1$ and $V_2$, and the denominator indicates the product between the norm (length) of the vector $V_1$ and the norm of the vector $V_2$.

Returning to FIG. 2, a result output unit (output unit) 208 outputs, as a search result, the images having the calculated spatial distances shorter than a predetermined value, in ascending order of their spatial distance. It can be determined that an image having a shorter spatial distance has a higher similarity to the newly acquired image. It is thus possible to select appropriate medical treatment by referring to the similar images taken in the past.

Figure 9:
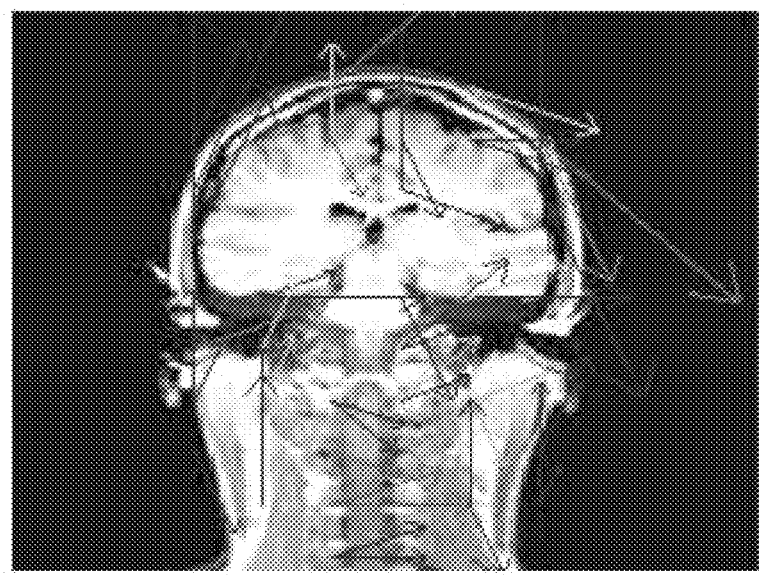
FIG. 9 shows an example of a search result display screen used in a medical image search apparatus according to an embodiment of the present disclosure.

It is noted that feature vectors may be overlaid on an image being displayed on the display device 23 as a search result. FIG. 9 shows an example of a search result display screen used in the medical image search apparatus 1 according to one embodiment.

As shown in FIG. 9, a past image that has been determined to be most similar to the acquired image is displayed and, of the wavelet features, those greater than a predetermined value are displayed overlaid on the image as the feature vectors. The length of each arrow indicates the magnitude of the feature value. The direction of each arrow indicates the one of the eight directions in which the feature value is greatest. The scales may also be distinguished by colors, line types, and so on.

Figure 10:
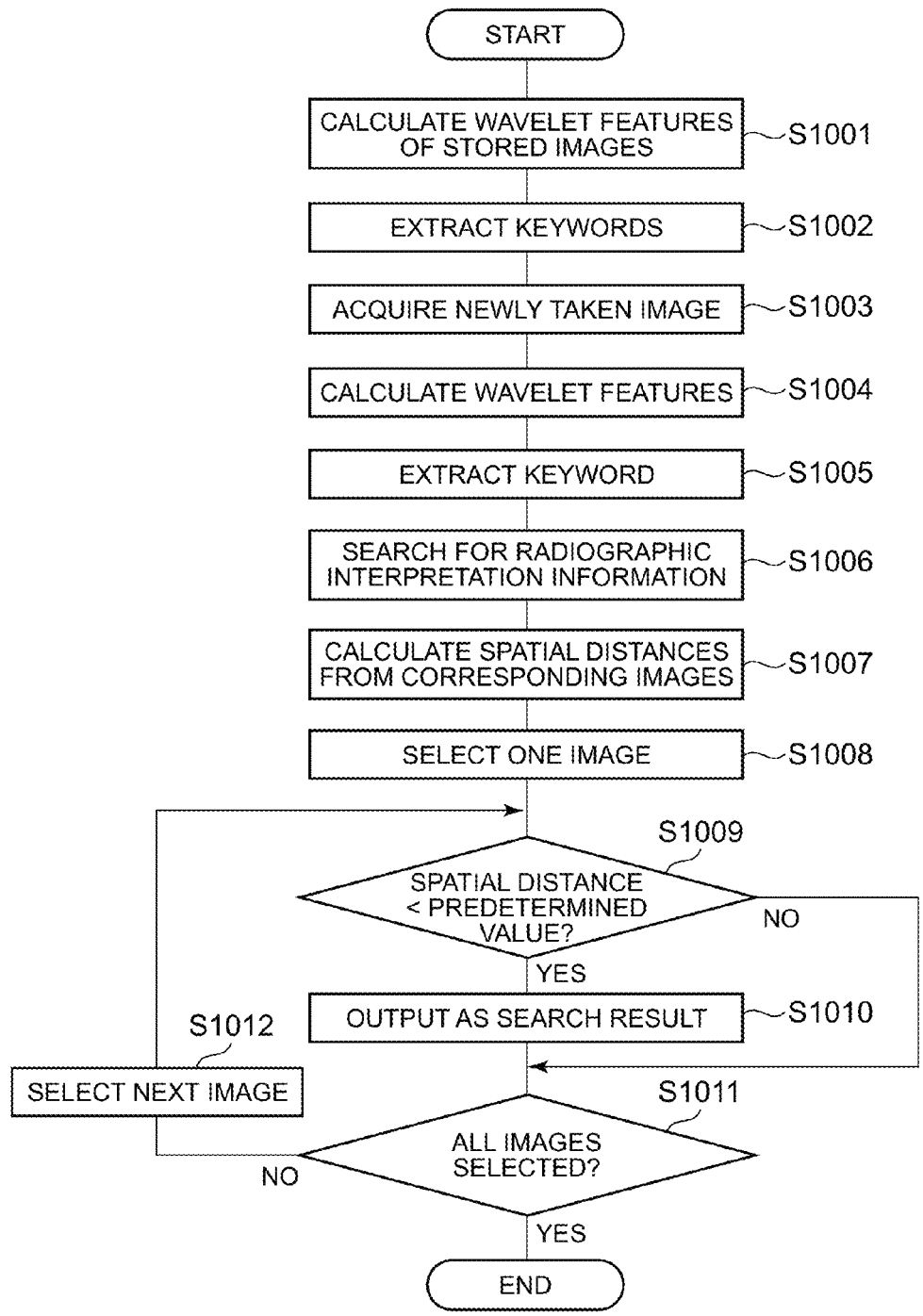
FIG. 10 is a flowchart illustrating a processing procedure of a CPU in a medical image search apparatus according to an embodiment of the present disclosure.

FIG. 10 is a flowchart illustrating the processing procedure of the CPU 11 in the medical image search apparatus 1 according to an embodiment. Referring to FIG. 10, the CPU 11 in the medical image search apparatus 1 calculates wavelet features of a plurality of images that have been taken and stored in the past (S1001). In the present embodiment, Gabor wavelet features are calculated as the wavelet features.

The CPU 11 extracts keywords included in the radiographic interpretation information for each of the stored past images (S1002), and stores the extracted keywords and the wavelet features calculated in the above-described manner, in association with the stored past images.

The CPU 11 acquires a newly taken image, in association with radiographic interpretation information (S1003), calculates wavelet features of the acquired image in the above-described manner (S1004), and stores the calculated wavelet features as visual words in the visual word storage unit 133.

The CPU 11 extracts at least one keyword included in the radiographic interpretation information for that acquired image (S1005), and on the basis of the extracted keyword, searches for similar radiographic interpretation information from the stored keywords (S1006). This makes it possible to effectively narrow down the images to be searched for a similar image.

The CPU 11 calculates a wavelet feature-based spatial distance between the acquired image and each of a plurality of images corresponding to the radiographic interpretation information found (S1007). The CPU 11 selects one of the images corresponding to the radiographic interpretation information found (S1008), and determines whether the spatial distance calculated for the selected image is shorter than a predetermined value (S1009).

If the CPU 11 determines that it is shorter than the predetermined value (YES in S1009), the CPU 11 determines that the image is similar, and outputs the image as a search result (S1010). At this time, the CPU 11 outputs the images that have been determined to be similar, in ascending order of their spatial distance. For example, the image(s) is/are output to the display device 23 for display.

If the CPU 11 determines that the spatial distance calculated is not shorter than the predetermined value (NO in S1009), the CPU 11 determines that the image is not similar, in which case S1010 is skipped. The CPU 11 determines whether all the images have been selected (S1011). If the CPU 11 determines that there is an image yet to be selected (NO in S1011), the CPU 11 selects a next image (S1012). The process then returns to S1009, and the above-described processing is repeated. If the CPU 11 determines that all the images have been selected (YES in S1011), the CPU 11 terminates the processing.

As described above, according to the present embodiment, the wavelet features indicating the features of an acquired medical image can be used to search for a similar image from among the images stored as past cases. Even an inexperienced doctor is able to find an image that corresponds to the most similar case and, thus, to select appropriate medical treatment.

It is noted that the present invention is not restricted to the above-described embodiment; a variety of modifications and improvements are possible within the scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the invention has been described with reference to exemplary embodiments, it will be understood by those skilled in the art that various changes may be made and equivalents may be substituted for elements thereof without departing from the scope of the invention. In addition, many modifications may be made to adapt a particular system, device or component thereof to the teachings of the invention without departing from the essential scope thereof. Therefore, it is intended that the invention not be limited to the particular embodiments disclosed for carrying out this invention, but that the invention will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A method of searching for an image similar to a newly taken image from among medical images based on past cases, comprising:
   calculating, using a computer system, wavelet features of a plurality of images that have been taken and stored in the past;
   extracting, using the computer system, a keyword included in radiographic interpretation information for each stored image;
   storing, using the computer system, the calculated wavelet features and the extracted keywords in association with the respective stored images;
   acquiring, using the computer system, a newly taken image;
   calculating, using the computer system, a wavelet feature of the acquired image;
   extracting, using the computer system, a keyword included in radiographic interpretation information corresponding to the acquired image and, on the basis of the extracted keyword, searching for similar radiographic interpretation information from the stored keywords;
   calculating, using the computer system, a wavelet feature-based spatial distance between the acquired image and each of images corresponding to the radiographic interpretation information found; and
   outputting, using the computer system, as a search result, any images for which the calculated wavelet feature-based spatial distance is shorter than a predetermined value, in ascending order of the calculated wavelet feature-based spatial distance.

2. The method of claim 1, wherein the wavelet features are two-dimensional Gabor wavelet features.

3. The method of claim 1, further comprising:
   calculating, using the computer system, frequency distribution vectors for all images, by calculating M said wavelet features for each image and binarizing the respective wavelet features for conversion into an M-dimensional bit string, wherein the calculated wavelet feature-based spatial distance is calculated as an angle between the calculated frequency distribution vectors, and wherein M is a natural number of 2 or greater.

* * * * *